US006753414B2

(12) United States Patent
Jin et al.

(10) Patent No.: US 6,753,414 B2
(45) Date of Patent: Jun. 22, 2004

(54) PROCESS FOR PREPARING SAPONIN COMPOUNDS

(75) Inventors: Zhendong Jin, Coralville, IA (US); Wensheng Yu, Fords, NJ (US)

(73) Assignee: University of Iowa Research Foundation, Inc., Iowa City, IA (US)

( * ) Notice: Subject to any disclaimer, the term of this patent is extended or adjusted under 35 U.S.C. 154(b) by 0 days.

(21) Appl. No.: 10/213,363

(22) Filed: Aug. 6, 2002

(65) Prior Publication Data
US 2003/0069214 A1 Apr. 10, 2003

Related U.S. Application Data
(60) Provisional application No. 60/310,709, filed on Aug. 7, 2001.

(51) Int. Cl.$^7$ .............................. C07H 1/00; C07J 53/00
(52) U.S. Cl. ........................................ 536/5; 552/502
(58) Field of Search .............................. 536/5; 552/502

(56) References Cited
U.S. PATENT DOCUMENTS

| | | | |
|---|---|---|---|
| 4,501,734 A | 2/1985 | Tanaka et al. | 514/198 |
| 4,938,949 A | 7/1990 | Borch et al. | 424/10 |
| 5,057,540 A | 10/1991 | Kensil et al. | 514/25 |
| 5,118,671 A | 6/1992 | Bombardelli et al. | 514/26 |
| 5,147,859 A | 9/1992 | Bombardelli et al. | 514/26 |
| 5,166,139 A | 11/1992 | Bombardelli et al. | 514/26 |
| 6,355,816 B1 * | 3/2002 | Dobbins | 554/14 |

OTHER PUBLICATIONS

Alexakis, A , et al., "Organocopper conjugate addition reaction in the presence of trimethylchlorosilane", *Tetrahedron Letters, 27*(9), (1986), 1047–1050.
Andringa, H. , et al., "An Alternative Procedure for the O–Trimethylsilylation of Enolates Generated by Copper–Catalyzed 1,4–Additions", *Synthetic Communications*, vol. 21, Nos. 12 & 13,(1991), 1393–1396.
Corey, E J., et al., "The reactions of combined organocuprate– chlorotrimethylsilane reagents with conjugated carbonyl compounds", *Tetrahedron Letters, 26*(49), (1985), 6019–6022.
Davis, Franklin A., et al., "Applications of oxaziridines in organic synthesis", *Tetrahedron, 45*(18), (1989),5703–5742.
Deng, Shaojiang , et al., "First Total Synthesis of an Exceptionally Potent Antitumor Saponin, OSW–1", *Journal of Organic Chemistry, 64*(1), (Jan. 8, 1999),202—208.
Duhamel, Pierre , et al., "Unprecedented route to enolates from silyl enol ethers and enol acetates: reaction with hard and soft electrophiles", *Journal of the Chemical Society, Perkins Transactions 1,*, (1993),2509–2511.
Guo, Chuangxing , et al., "The first synthesis of the aglycone of the potent anti–tumor steroidal saponin OSW–1", *Tetrahedron Letters, 39*(10), (Mar. 5, 1998), 1099–1102.

Jiang, Zi–Hua , et al., "Synthesis of the hexasaccharide moiety of pectinioside E", *Liebigs Annalen der Chemie, 9*, (1992),975–982.
Kubo, Satoshi , et al., "Acylated cholestane glycosides from the bulbs of Ornithogalum saundersiae", *Phytochemistry, 31*(11), (1992),3969–3973.
Lipshutz, Bruce H., "Applications of High r Order Mixed Organocuprates to Organic Synthesis", *Synthesis, 4*, (Apr. 1987),325–341.
Mimaki, Yoshihiro , et al., "Cholestane glycosides with potent cytostatic activities on various tumour cells from Ornithogalum saundersiae bulbs", *Bioorganic & Medicinal Chemistry Letters, 7*(5), (1997),633–636.
Morzycki, Jacek W., et al., "Some reactions of 16 ,17 – oxido–steroids: a study related to the synthesis of the potent anti–tumor Saponin OSW–1 aglycone", *Tetrahedron Letters, 41*(9), (May 6, 2000),3751–3754.
Moyano, Albert , et al., "Simple preparation of chiral acetylenic ethers", *Journal of Organic Chemistry, 52*(13), (Jun. 26, 1987),2919—2922.
Nicolaou, K C., et al., "Design, Synthesis and Biological Evaluation of Carbohydrate–Based Mimetics of cRGDFV", *Tetrahedron, 53*(26), (Jun. 30, 1997),8751–8778.
Nicolaou, K C., et al., "Total Synthesis of Eleutherobin and Eleuthosides A and B", *Journal of the American Chemical Society, 120*(34), (Sep. 2, 1988),8674—8680.

(List continued on next page.)

Primary Examiner—Elli Peselev
(74) Attorney, Agent, or Firm—Schwegan, Lundberg, Woessner & Kluth, P.A.

(57) ABSTRACT

A process for preparing compounds of formula (1):

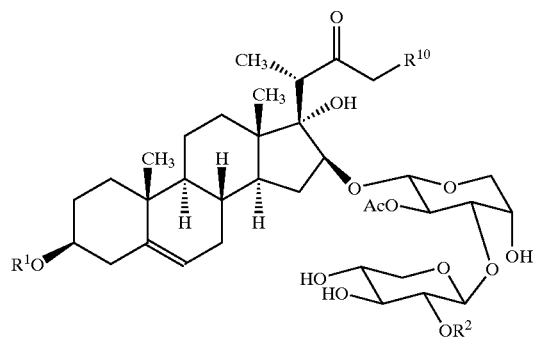

including the convergent steps as defined in the specification, and wherein R groups have any of the values defined in the specification. The invention also provides processes and intermediates useful for preparing compounds of formula (1).

22 Claims, No Drawings

OTHER PUBLICATIONS

Pereira, O., et al., "Trimethylstannylvinyl cuprates—Generation and 1,4–Conjugate Addition to Alpha, Beta–Unsaturated Ketones", *Tetrahedron Letters*, vol. 36, No. 48,(1995),8749–8752.

Sashida, Y, et al., "Steroidal saponins from *Smilax riparia* and *S. china*", *Phytochemistry, 31*(7), (Jul. 1992), 2439–43.

Schmuff, Norman R., et al., "Organocuprate–mediated methods for the stereospecific introduction of steroid side Chains at C–20", *Journal of Organic Chemistry*, vol. 48, No. 9, (May 6, 1983), 1404—1412.

William, Anthony D., et al., "A Method to Accomplish a 1,4–Addition Reaction of Bulky Nucleophiles to Enones and Subsequent Formation of Reactive Enolates", *Org. Lett.*, vol. 3, No. 13,(05 24 2001),2017–2020.

Yu Wensheng, et al., "A facile generation of enolates from silyl enol ethers by potassium ethoxide", *Tetrahedron Letters, 42*(3), (Jan. 15, 2001),369–372.

Yu, Wensheng, et al., "A Highly Stereoselective Synthesis of –Halo Vinyl Ethers and Their Applications in Organic Synthesis", *Journal of the American Chemical Society, 122*(40), (Oct. 11, 2000),9840—9841.

* cited by examiner

PROCESS FOR PREPARING SAPONIN COMPOUNDS

RELATED APPLICATION

This application claims priority under 35 U.S.C. 119(e) from U.S. Provisional Application No. 60/310,709 filed Aug. 7, 2001, which application is incorporated herein by reference.

FIELD OF THE INVENTION

The present invention provides processes for the preparation of saponin compounds, and more specifically, provides processes for the preparation of compounds of formula (1) and to intermediates leading thereto as described herein. The compounds of formula (1) are related to naturally occurring saponins such as OSW-1 and analogues thereof. The compounds are useful as anti-cancer drugs.

BACKGROUND OF THE INVENTION

Saponins are a large family of naturally occurring glycoconjugate compounds with considerable structural diversity. Saponin OSW-1, 3β,16β,trihydroxycholest-5-en-22-one 16-O-{O-(2-O-(4-methoxybenzoyl)-β-D-xylopryanosyl)-(1-3)-2-O-acetyl-α-arabinopryanoside, is the major component of a small group of cholestane saponins isolated by Sashida et al. (*Phytochemistry*, 31, 3936, 1992.) from the bulbs of a species of the lily family. OSW-1 is highly toxic against a broad spectrum of malignant tumor cells (Bioorg., Med. Chem. Lett., 7, 633, 1997.) with little toxicity to normal cells in vitro.

Saponins are glycosidic natural plant products, composed of a ring structure (the aglycone) to which is attached one or more sugar chains. The saponins are grouped together based on several common properties. In particular, saponins are surfactants which display hemolytic activity and form complexes with cholesterol. Although saponins share these properties, they are structurally diverse. In particular, the aglycone can be a steroid, triterpenoid or a steroidal alkaloid and the number of sugars attached to the glycosidic bonds vary greatly.

Saponins have been employed as absorption adjuvants in pharmaceutical compositions. For example, U.S. Pat. No. 4,501,734, describes the use of a triterpenoid saponin extract from *Sapindus mukurossi Gaertn.* to increase absorption of a coadministered beta-lactam antibiotic. Saponins have also been used as immunological adjuvants in vaccine compositions against a variety of diseases including protozoal infections and foot and mouth disease. The saponins typically used as immunological adjuvants are triterpene glycosides extracted from the South American tree, Quillaja saponaria, termed Quil A., see for example, U.S. Pat. No. 5,057,540.

Saponins have also been used in pharmaceutical compositions for a variety of other purposes. For example, U.S. Pat. No. 5,118,671, describes the use of aescin, a saponin obtained from *Aesculus hippocastanum* seeds, in pharmaceutical and cosmetic compositions as an anti-inflammatory. Similarly, U.S. Pat. No. 5,147,859, discusses the use of *Glyccyrrhiza glabra* saponin/phospholipid complexes as anti-inflammatory and anti-ulcer agents and U.S. Pat. No. 5,166,139, describes the use of complexes of saponins and aglycons, obtained from *Centella asiatica* and Terminalia sp., with phospholipids in pharmaceutical compositions. International Publication No. WO 91/04052, published 4 Apr. 1991, discusses the use of solid Quillaja saponaria saponin/GnRH vaccine compositions for immunocastration and immunospaying.

Methods for the synthesis of saponins, and OSW-1 particularly, have received considerable attention recently. Fuchs et al., reported the synthesis of the aglycone portion of OSW-1 (*Tetrahedron Lett.*, 39, 1099, 1998.). Hui et al., reported a convergent total synthesis of OSW-1 from commercially available dehydroisoandrosterone, L-arabinose, and D-xylose in 27 steps in a 6 percent overall yield. (*J. Org. Chem.*, 64, 202, 1999.)

In view of the potential of saponin compounds to treat cancer and related diseases, and the limitations of currently available synthetic methodology, a need exists for efficient processes for the preparation of naturally occurring saponins such as OSW-1 and analogues thereof.

SUMMARY OF THE INVENTION

In accordance with the present invention, processes are provided to prepare naturally occurring saponins such as OSW-1 and analogues thereof, having useful biological activity, and particularly activity as anti-cancer agents. Thus, the present invention provides, in embodiments, a process for preparing the compound of formula (1):

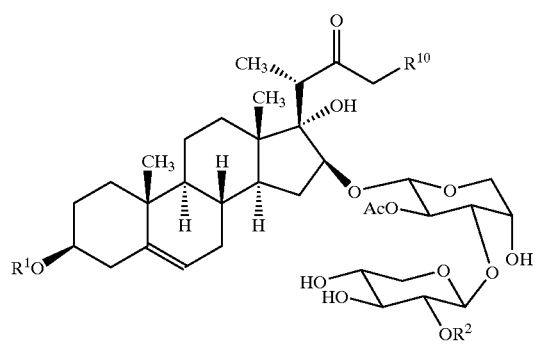

wherein $R^1$ is independently H or a hydroxyl protecting group, $R^2$ is independently -C(=O)-Ar or -C(=O)-$CR_c$=$CR_d$-Ar, wherein Ar is independently aryl or heteroaryl, and $R_c$ and $R_d$ are each independently —H, $C_{1-6}$alkyl, $C_{1-6}$alkanoyl, $C_{1-6}$alkoxycarbonyl, aryl, (aryl)$C_{1-6}$alkyl, arylcarbonyl, or aryloxycarbonyl, and $R^{10}$ is, for example, $C_{1-12}$ alkyl, preferably $C_{2-6}$ alkyl, and most preferably —$CH_2$—$CH(CH_3)_2$, such as, a compound of the formula

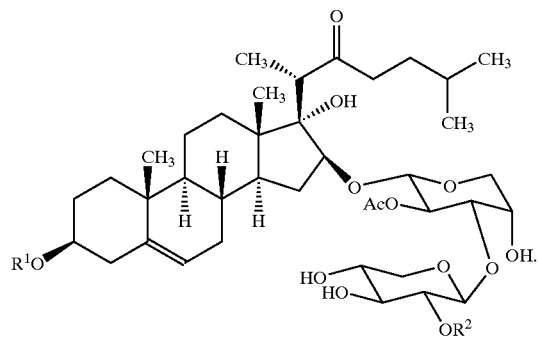

The present invention also provides a process for preparing a saponin intermediate comprising:

reacting, in the presence of a 1,4-addition activating agent, an enone compound of the formula (9)

9

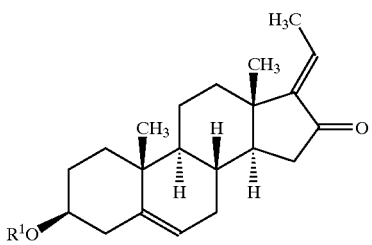

wherein $R^1$ is independently —H or a hydroxyl protecting group, with an alpha-alkoxy vinyl cuprate compound of the formula (8):

8

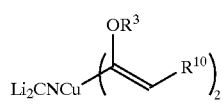

wherein $R^3$ is an enolic hydroxyl protecting group and $R^{10}$ is, for example, $C_{1-12}$ alkyl, preferably $C_{2-6}$ alkyl, and most preferably —$CH_2$—$CH(CH_3)_2$ wherein the compound of the formula (8) is:

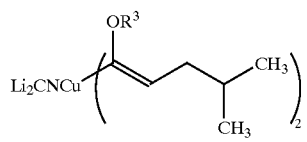

wherein $R^3$ is an enolic hydroxyl protecting group, to form a compound of the formula (18):

18

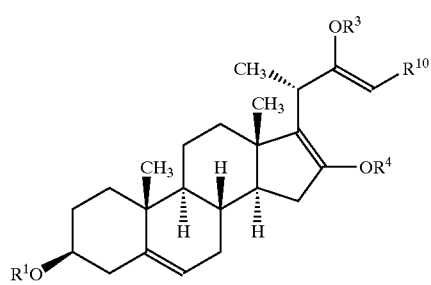

wherein $R^4$ is an enolic hydroxyl protecting group, for example, with chemical lability or stability different from the aforementioned $R^3$ enolic hydroxyl protecting group, and $R^{10}$ is as defined above. Preferably $R^{10}$ is —$CH_2$—$CH(CH_3)_2$, such as, in the compound of the formula:

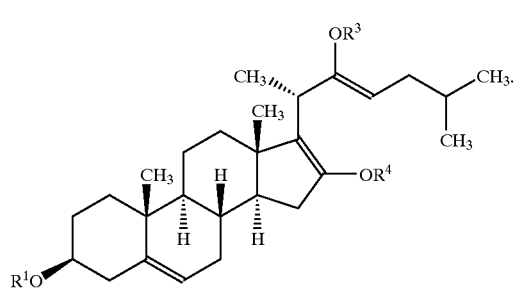

The preparative processes of the present invention can also further comprise:
a) converting the above vinyl ether of compound (18) at —$OR^3$ to a corresponding ketal;
b) generating a corresponding enolate at —$OR^4$ of compound (18) wherein $R^4$ is, for example, a metal counter ion; and c) oxidizing the resulting enolate to an alpha-hydroxy ketone compound of the formula (20):

20

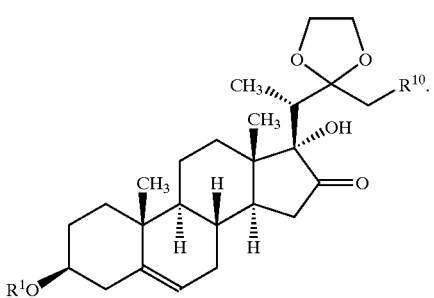

The foregoing preparative process of the present invention can further comprise: stereoselectively reducing the ketone of the formula (20) to a 1,2-diol compound of formula (7):

7

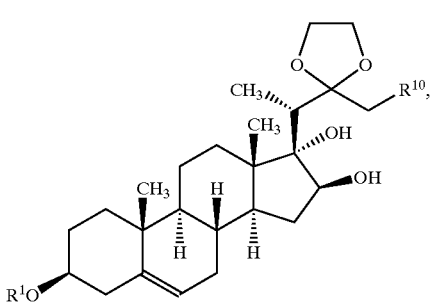

for example, of the formula:

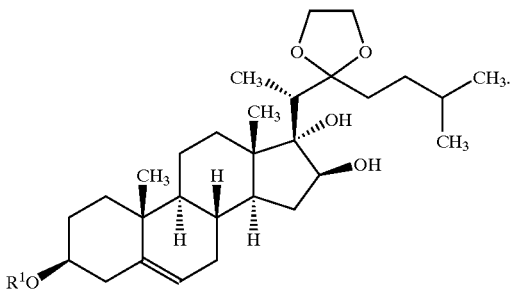

In other embodiments, the present invention provides a process for preparing the compound of formula (1):

1

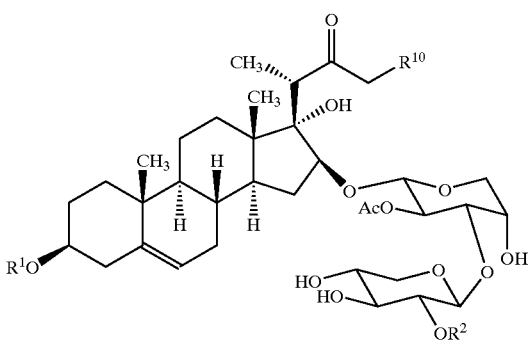

wherein $R^1$ can be independently —H or a hydroxyl protecting group, and $R^2$ can be independently —C(=O)—Ar or —C(=O)—$CR_c$=$CR_d$—Ar, wherein Ar can be independently aryl or heteroaryl, and $R_c$ and $R_d$ can independently each be —H, $C_{1-6}$alkyl, $C_{1-6}$alkanoyl, $C_{1-6}$alkoxycarbonyl, aryl, (aryl)$C_{1-6}$alkyl, arylcarbonyl, or aryloxycarbonyl, and $R^{10}$ is as defined above, comprising:

a) coupling a compound of the formula (7) prepared in accordance with the above description and as illustrated herein:

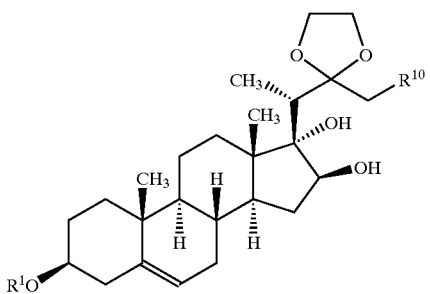

7 with a compound of the formula (6):

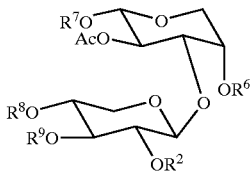

6 wherein $R^6$, $R^8$ and $R^9$ are each independently a hydroxyl protecting group, and —$OR^7$ is a leaving group, that is, a displaceable group which can be substituted by another group or molecule, such as by the secondary alcohol (—OH) functional group of compound (7), and without inversion of the stereochemistry on the sugar ring carbon to which —$OR^7$ is attached, to form a compound of the formula (36); and

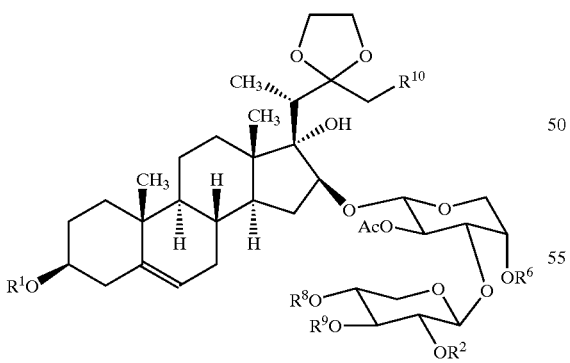

36 b) deprotecting the compound of formula (36) to afford the compound of formula (1).

In embodiments, the aforementioned $R^1$ as a hydroxyl protecting group can be, for example, of the formula —Si($R^{12}$)$_3$ wherein each $R^{12}$ can be independently $C_{1-4}$ alkyl, such as —Me, —Et, and the like. The Ar of —C(=O)—Ar can be independently an aryl or a heteroaryl group, optionally substituted with one or more substituents selected independently from, for example, halo, —OH, —CN, —$NO_2$, —$CF_3$, —$OCF_3$, methylene dioxy, $C_{1-6}$alkyl, $C_{1-6}$alkoxy, phenyl, $NR_cR_d$, or —C(=O)$NR_cR_d$; wherein each $R_c$ and $R_d$ is independently —H, $C_{1-6}$alkyl, $C_{1-6}$alkanoyl, $C_{1-6}$alkoxycarbonyl, aryl, (aryl)$C_{1-6}$alkyl, arylcarbonyl, aryloxycarbonyl, or like groups; or $R_c$ and $R_d$ together with a nitrogen to which they are attached form a pyrrolidino, piperidino, morpholino, or thiomorpholino ring; or a pharmaceutically acceptable salt thereof.

The Ar of —C(=O)—$CR_c$=$CR_d$—Ar can independently be an aryl or a heteroaryl group and wherein any aryl or heteroaryl can be optionally substituted with one or more substituents independently selected from halo, —OH, —CN, —$NO_2$, —$CF_3$, —$OCF_3$, methylene dioxy, $C_{1-6}$alkyl, $C_{1-6}$alkoxy, phenyl, $NR_cR_d$, —C(=O)$NR_cR_d$, and like groups; wherein each $R_c$ and $R_d$ can be independently hydrogen, $C_{1-6}$alkyl, $C_{1-6}$alkanoyl, $C_{1-6}$alkoxycarbonyl, aryl, (aryl)$C_{1-6}$alkyl, arylcarbonyl, aryloxycarbonyl, or like groups; or $R_c$ and $R_d$ together with the nitrogen to which they are attached form a pyrrolidino, piperidino, morpholino, thiomorpholino ring, and like groups; or a pharmaceutically acceptable salt thereof. In embodiments, $R^2$ can be independently p-methoxybenzoyl, 3,4-dimethoxybenzoyl, (E)-cinnamoyl, or (Z)-cinnamoyl, and like groups.

Preferred $R^1$ and $R^2$ groups in the compound of the formula (1) are where $R^1$ is —H, and $R^2$ is p-methoxybenzoyl, and which compound corresponds to OSW-1 wherein $R^{10}$ is —$CH_2$—CH($CH_3$)$_2$. The 1,4-addition activating agent can be, for example, a trialkylsilylchloride, such as trimethylsilylchloride. The $R^3$ enolic hydroxyl protecting group can be, for example, an alkyl group and like groups, and preferably a bulky alkyl or cycloalkyl group, such as, $C_{5-7}$cycloalkyl, and the $R^4$ enolic hydroxyl protecting group can be, for example, alkanoyl, such as acetyl, and like groups.

The selective deprotection of indicated hydroxyl groups to afford the compound of formula (1) can be accomplished by sequentially treating the compound of formula (36) with DDQ and thereafter bis-(acetonitrile)dichloropalladium(II). The compound of the formula (9) can be prepared by the steps comprising, for example:

a) olefinating the ketone of the compound of formula (14), for example, with an appropriate Wittig reagent, like olefin producing ylid modification reagents, and like reagents or equivalent reagents which produce an olefin product being compatible with the $R^1$ protecting group;

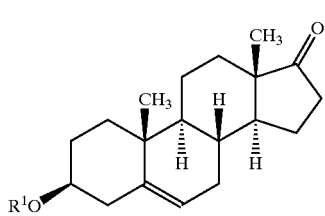

14 b) allylicly oxidizing the resulting olefin compound to form an allylic alcohol compound of formula (15); and

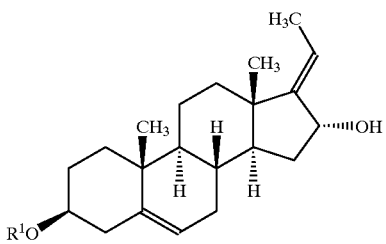

c) oxidizing the allylic alcohol (15) to form a 1,4-enone compound of formula (9)

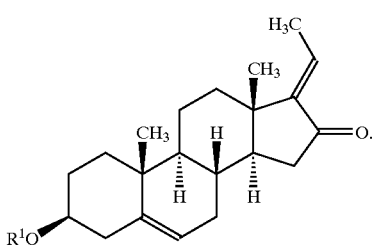

The compound of the formula (6):

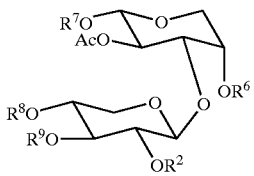

can be prepared by the steps comprising:

a) glycosylating a compound of the formula (25)

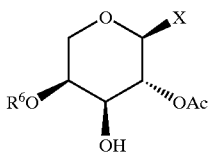

wherein $R^6$ is a hydroxyl protecting group, that is, suitable for protection and deprotection of a secondary hydroxyl group in a simple sugar or a similarly substituted pyranose ring system, and X can be, for example, an $SN_1$ leaving group, that is for example, a group which is capable of selective substitution or conversion to an —$OR^7$ leaving group and without stereochemical inversion at the sugar ring carbon. For example, X can be —SAr wherein Ar is, for example, phenyl. Compound 25 can be glycosylated, for example, by reaction with a compound of the formula (34)

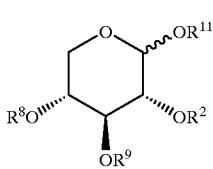

wherein —$OR^{11}$ is preferably a leaving group of the formula —OC(=NH)CCl$_3$, to afford a compound of the formula (35):

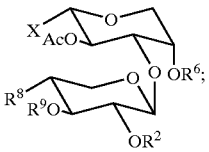

b) X is then converted into a leaving group —$OR^7$ of the formula, for example, —O—C(=NH)CCl$_3$ to afford the above compound of formula (6). The leaving group X can be, for example, —SAr wherein Ar is as defined above, such as phenyl, and like substituents.

The present invention also provides novel intermediates and processes as disclosed herein that are useful for preparing compounds of formula (1).

DETAILED DESCRIPTION OF THE INVENTION

Applicants have discovered a new and efficient convergent strategy for the total synthesis of OSW-1 and related saponin compounds including direct introduction of the complete carbon side chain of OSW-1 steroid precursors as shown in Scheme 1.

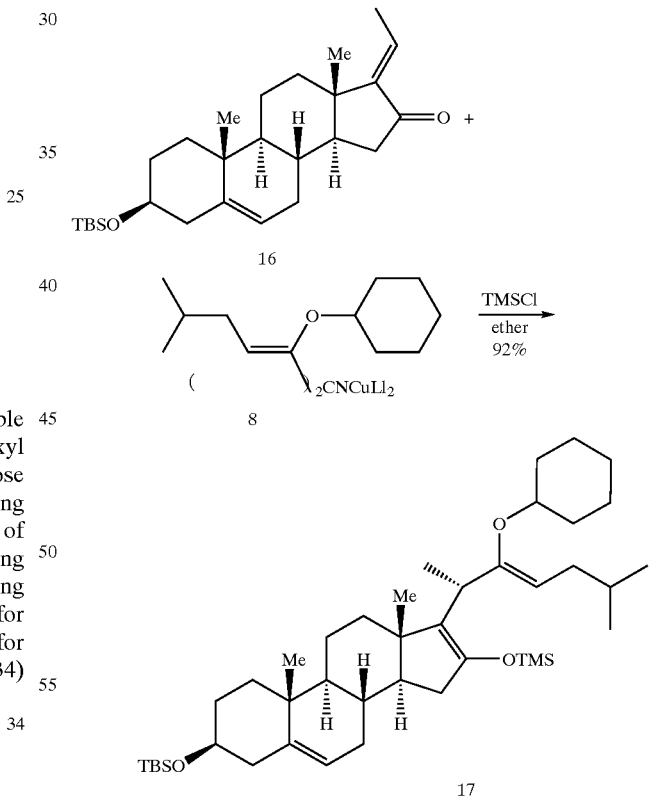

Scheme 1

A retrosynthetic analysis is shown in Scheme 2. OSW-1 (1) was conceptually disconnected into the disaccharide 6 and the steroid aglycone 7. Compound 7 was viewed as obtainable by 1,4-addition of the R-alkoxy vinyl cuprate 8 to compound 9 which compound was prepared from commercially available 5-androsten-3β-ol-17-one 10.

Scheme 2

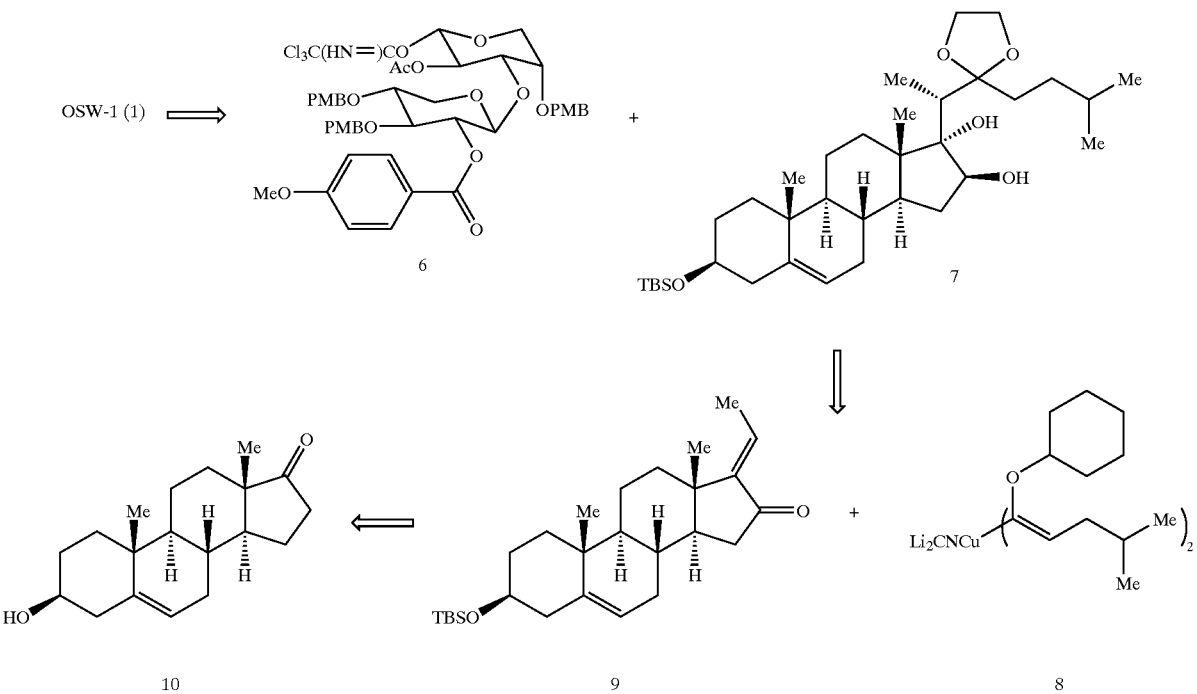

Scheme 3 outlines the synthesis of the R-alkoxy vinyl cuprate 8. The acetylenic ether 11 was prepared according to the literature procedure.[13] The α-bromo vinyl ether 13 was prepared regio- and stereoselectively according to literature procedures,[7] which was in turn converted in situ to a high-order cuprate 8.[14]

Scheme 3

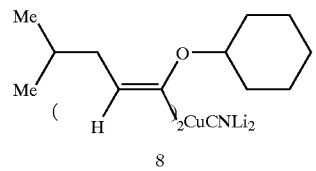

a. (i) n-BuLi, -20–0° C., 20 min; (ii) iso-butyl triflate, -30–25° C., 12 h, 85%;
b. b. TMSBr, MeOH, CH$_2$Cl$_2$, -40–25° C., 15 min, 99%:
c. c. (i) t-BuLi (2 equiv), ether, -78° C., 30 min; (ii) CuCN, LiCl, THF, -78° C., 15 min.

Compound 15 was prepared from 10 according to literature procedure as shown in Scheme 4.[15]

Scheme 4

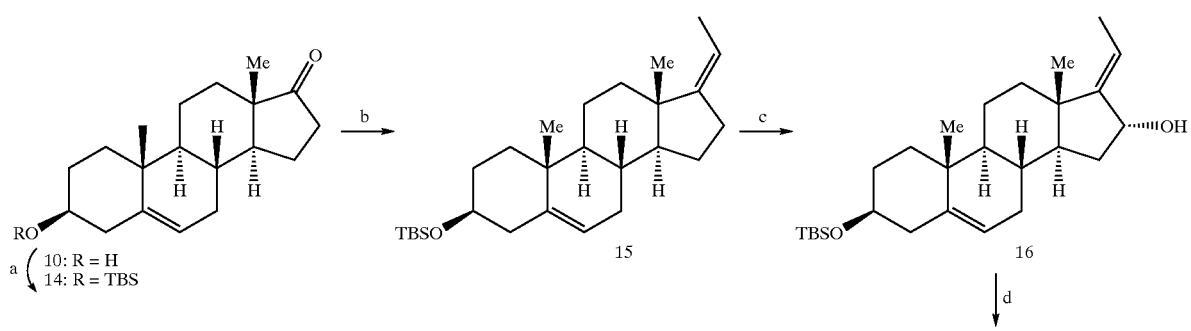

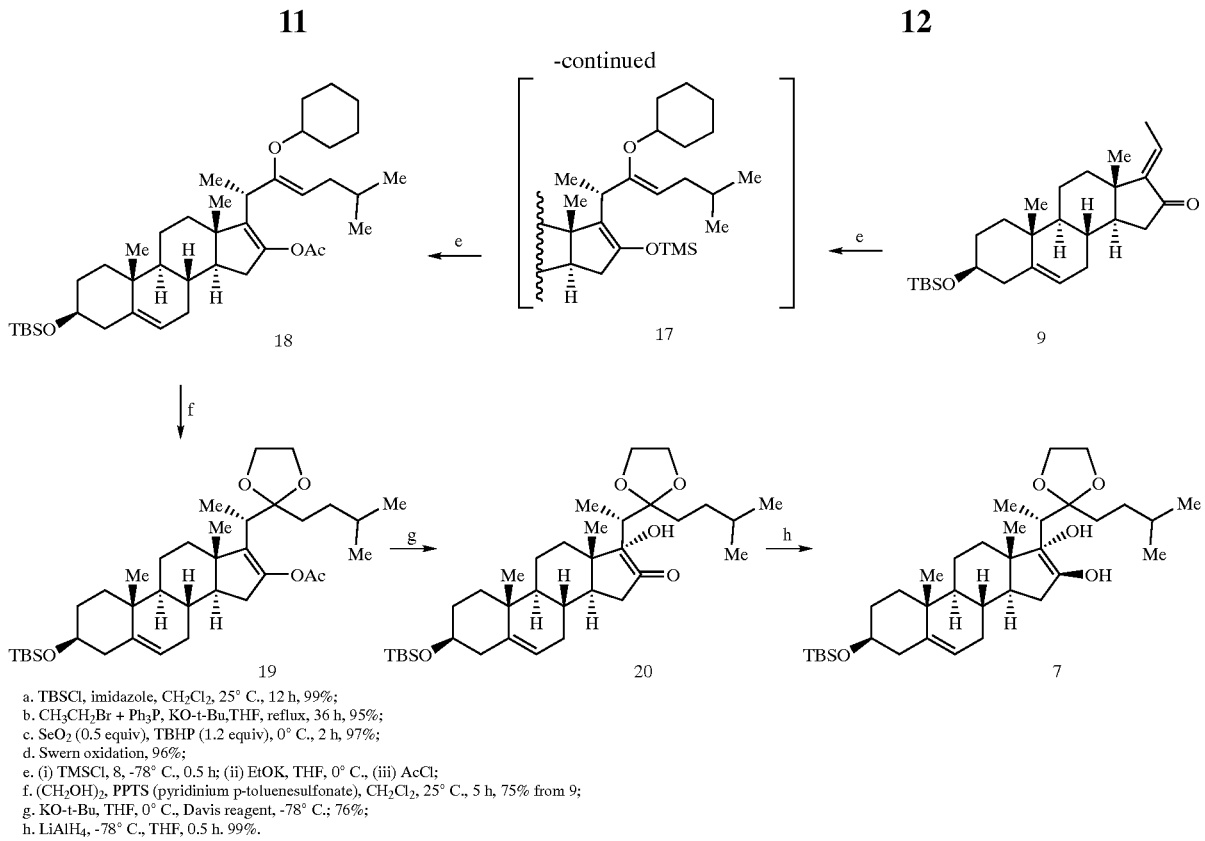

a. TBSCl, imidazole, CH$_2$Cl$_2$, 25° C., 12 h, 99%;
b. CH$_3$CH$_2$Br + Ph$_3$P, KO-t-Bu,THF, reflux, 36 h, 95%;
c. SeO$_2$ (0.5 equiv), TBHP (1.2 equiv), 0° C., 2 h, 97%;
d. Swern oxidation, 96%;
e. (i) TMSCl, 8, -78° C., 0.5 h; (ii) EtOK, THF, 0° C., (iii) AcCl;
f. (CH$_2$OH)$_2$, PPTS (pyridinium p-toluenesulfonate), CH$_2$Cl$_2$, 25° C., 5 h, 75% from 9;
g. KO-t-Bu, THF, 0° C., Davis reagent, -78° C.; 76%;
h. LiAlH$_4$, -78° C., THF, 0.5 h. 99%.

Trost and co-workers have shown that selenium dioxide-mediated allylic oxidation can regio- and stereoselectively introduce a hydroxy group into the C-16 of the steroid 17(20)-en-16-ones.[15] However, in their examples the double bond in the B ring was protected. The present invention achieves complete chemo-, regio-, and stereoselective allylic oxidation at C-16 under the same reaction conditions without the protection of the 5(6) double bond.

Swern oxidation of 16 afforded enone 9 in nearly quantitative yield.[15] TMSCl-activated[8] 1,4-addition of R-alkoxy vinyl cuprate 8 to enone 9 gave silyl enol ether intermediate 17, which was converted to enol acetate 18 in a single operation without the isolation of 17.[16] The conversion of silyl enol ether 17 to enol acetate 18 enabled chemoselective transformation of the enol ether to cyclic acetal 19. Generation of the enolate from 19 by potassium ethoxide or potassium tert-butoxide[17] followed by in situ oxidation by Davis reagent[18] stereoselectively gave R-hydroxy ketone 20 in 76% yield. Stereoselective reduction of compound 20 by LiAlH$_4$ at −78° C. provided the requisite trans-16β,17α-diol 7 in 97% yield.[19] Thus, the protected aglycone of OSW-1 (1) was synthesized with eight operations in 48.4% overall yield.

Synthesis of the disaccharide 6 is outlined in Schemes 5, 6, and 7. Thioglycoside 22 was prepared from tetraacetyl-L-arabinose 21 as shown in Scheme 5.

Scheme 5

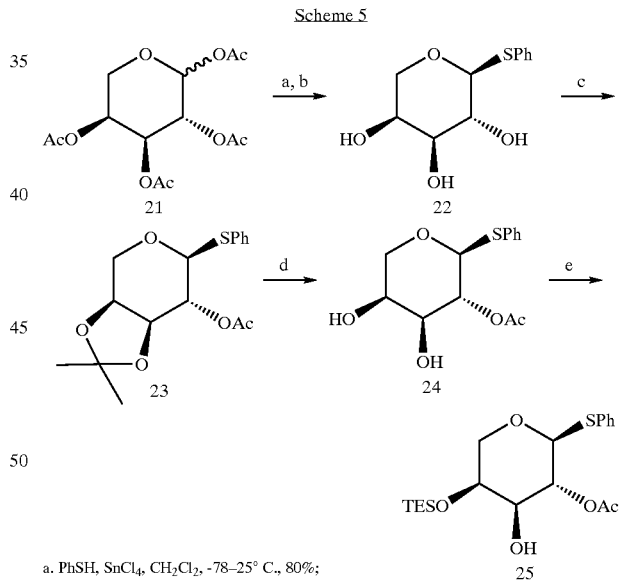

a. PhSH, SnCl$_4$, CH$_2$Cl$_2$, -78–25° C., 80%;
b. NaOMe, MeOH, 6 h, 95%;
c. (i) Me$_2$C(OMe)$_2$, CSA, CH$_2$Cl$_2$, 12 h; (ii) Ac$_2$O, DMAP, Et$_3$N, CH$_2$Cl$_2$, 2 h;
d. AMBERLITE IR-118H, MeOH, 12 h, 90% from 22;
e. TESOTf, lutidine, CH$_2$Cl$_2$, - 50 to -70° C., 2 h, 90%.

Regioselective protection of the cis-diol 22 followed by protection of the C-2 hydroxy group gave 23 in 90% yield. Deprotection of the acetonide afforded diol 24. Although it is known that the equatorial C-3 hydroxy group in many sugars is more reactive than C-4 axial hydroxy group, surprisingly high selectivity at the C-4 hydroxy group was observed when 24 was treated with TESOTf and lutidine at low temperature affording the desired product 25 in 90% yield.

The thio ortho ester 28 was prepared from tetraacetyl-D-xylose 26 as shown in Scheme 6.[20]

Scheme 6

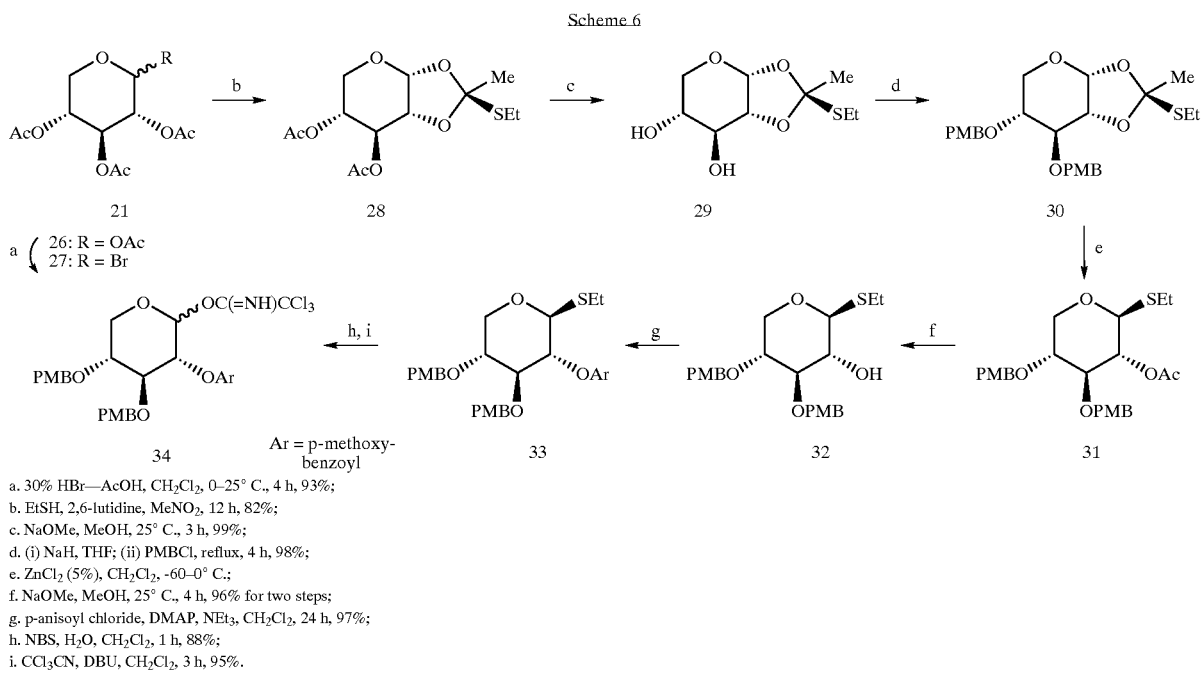

a. 30% HBr—AcOH, CH$_2$Cl$_2$, 0–25° C., 4 h, 93%;
b. EtSH, 2,6-lutidine, MeNO$_2$, 12 h, 82%;
c. NaOMe, MeOH, 25° C., 3 h, 99%;
d. (i) NaH, THF; (ii) PMBCl, reflux, 4 h, 98%;
e. ZnCl$_2$ (5%), CH$_2$Cl$_2$, -60–0° C.;
f. NaOMe, MeOH, 25° C., 4 h, 96% for two steps;
g. p-anisoyl chloride, DMAP, NEt$_3$, CH$_2$Cl$_2$, 24 h, 97%;
h. NBS, H$_2$O, CH$_2$Cl$_2$, 1 h, 88%;
i. CCl$_3$CN, DBU, CH$_2$Cl$_2$, 3 h, 95%.

Protecting-group manipulations followed by zinc chloride promoted intramolecular ring-opening of the thio ortho ester 30 gave thioglycoside 31 in excellent yield. After deacetylation, the p-methoxy benzoyl group was introduced, and 33 was converted to 34 in 84%.[21]

Glycosylation of 25 with 34 afforded the β-disaccharide 35 which was converted to 6 as shown in Scheme 7.

Scheme 7

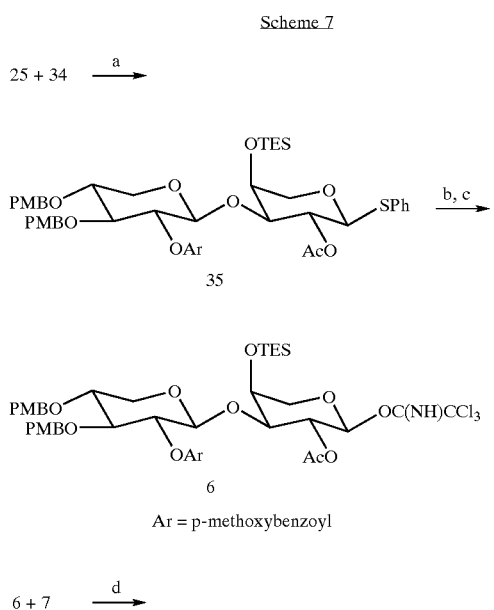

Ar = p-methoxybenzoyl

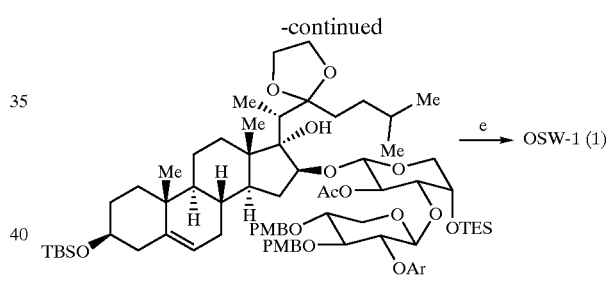

a. BF$_3$·Et$_2$O, 4 Å MS, CH$_2$Cl$_2$, -78 to -20° C., 2 h, 93%;
b. NBS, pyr, acetone-H$_2$O (9:1), 25° C., 2 h, 81%;
c. CCl$_3$CN, DBU, CH$_2$Cl$_2$, 12 h, 88%;
d. TMSOTf, 4 Å MS, CH$_2$Cl$_2$, -20–0° C., 30 min, 71%;
e. DDQ, CH$_2$Cl$_2$—H$_2$O, 25° C., 12 h; then, Pd(CN)$_2$Cl$_2$, acetone-H$_2$O, 25° C., 2 h, 81%.

Coupling of 6 with the steroid aglycone 7 under standard conditions[22] gave compound 36 in 71% yield. Removal of all of the protecting groups by sequential treatment of compound 36 with DDQ and bis-(acetonitrile)dichloropalladium(II) in one operation afforded OSW-1 (1) in 81% yield. The physical data of synthetic OSW-1 (1) were identical to those reported by Sashida.[10]

The new strategy provides stereoselective introduction of the steroid side chain via 1,4-addition of an α-alkoxy vinyl cuprate to 17(20)-en-16-one steroids. On the basis of the strategy, the highly potent anti-tumor natural product OSW-1 (1) was synthesized in 10 linear operations from 10 in 28% overall yield.

Additional supporting experimental information, such as spectral characterizations, is available at http://pubs.acs.org. The foregoing literature references of this section are listed below.

References

7) Yu, W.; Jin, Z. *J. Am. Chem. Soc.*, 122, 9840, 2000.
8) (a) Corey, E. J.; Boaz, N. W. *Tetrahedron Lett.*, 26, 6019, 1985.
   (b) Alexakisss, A.; Berlan, J.; Besace, Y. *Tetrahedron Lett.*, 27, 1047, 1986.
10) Kubo, S.; Mimaki, Y.; Terao M.; Sashida, Y.; Nikaido, T.; Ohmoto, T. *Phytochemitstry*, 31, 3969, 1992.
12) (a) Guo, C.; Fuchs, P. *Tetrahedron Lett.*, 39, 1099, 1998. (b) Deng, S.; Yu, B.; Lou, Y.; Hui, Y. *J. Org. Chem.*, 64, 202, 1999. (c) Morzycki, J. W.; Gryszkiewicz, A.; Jastrzebska, I. *Tetrahedron Lett.*, 41, 3751, 2000.
13) Moyano, A.; Charbonnier, F.; Greene, A. E. *J. Org. Chem.*, 52, 2919, 1987.
14) Lipshutz, B. H. *Synthesis*, 87, 325, 1987, and references therein.
15) Schmuff, N. R.; Trost, B. M. *J. Org. Chem.*, 48, 1404, 1983.
16) The stereochemistry at C-16 and C-17 of compound 7 was determined by NOESY spectra.
17) Nicolaou, K. C.; Trujillo, J. I.; Chibale, K. *Tetrahedron*, 53, 8751, 1997.
18) Yu, W.; Jin, Z. *Tetrahedron Lett.*, 42, 369, 2001.
19) Duhamel, P.; Cahard, D.; Poirier, J. M. *J. Chem. Soc., Perkin Trans.* 1, 21, 2509, 1993.
20) Davis, F. A.; Sheppard, A. C. *Tetrahedron*, 45, 5703, 1989.
21) Nicolaou, K. C.; Ohshima, T.; Hosokawa, S.; van Delft, F. L.; Vourloumis, D.; Xu, J. Y.; Pfefferkorn, J.; Kimet, S. *J. Am. Chem. Soc.*, 120, 8674, 1998.
22) Jiang, Z. H.; Schmidt, R. R. *Liebigs Ann. Chem.*, 975, 1992.

The following definitions are used, unless otherwise described: halo is fluoro, chloro, bromo, or iodo. Alkyl, alkoxy, and the like, denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more, for example, 1, 2, 3, or 4, double or triple bonds in the chain.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl, or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms, for example, by resolution of the racemic form by recrystallization techniques, by synthesis from optically-active starting materials, by chiral synthesis, or by chromatographic separation using a chiral stationary phase, and how to determine anticancer activity using the standard tests which are well known in the art.

The carbon atom content of various hydrocarbon-containing moieties is indicated by a prefix designating the minimum and maximum number of carbon atoms in the moiety, that is, the prefix $C_{i-j}$ indicates a moiety of the integer "i" to the integer "j" carbon atoms, inclusive. Thus, for example, $C_{1-6}$alkyl refers to alkyl of one to six carbon atoms, inclusive.

The compounds of the present invention are generally named according to the IUPAC or CAS nomenclature system. Abbreviations which are well known to one of ordinary skill in the art may be used, for example, "Ph" for phenyl, "Me" for methyl, "Et" for ethyl, "h" for hour or hours and "rt" for room temperature.

Specific and preferred values listed below for radicals, substituents, and ranges, are for illustration only; they do not exclude other defined values or other values within defined ranges for the radicals and substituents.

Specifically, $C_{1-4}$alkyl can be methyl, ethyl, propyl, isopropyl, butyl, iso-butyl, sec-butyl, and all isomers thereof; $C_{1-6}$alkyl can be methyl, ethyl, propyl, isopropyl, butyl, iso-butyl, sec-butyl, pentyl, 3-pentyl, hexyl, and all isomers thereof; $C_{1-6}$alkoxy can be methoxy, ethoxy, propoxy, isopropoxy, butoxy, iso-butoxy, sec-butoxy, pentoxy, 3-pentoxy, hexyloxy, and all isomers thereof; $C_{1-6}$alkanoyl can be, for example, acetyl, propanoyl, butanoyl, pentanoyl, 4-methylpentanoyl, hexanoyl, and all isomers thereof; $C_{1-6}$alkoxycarbonyl can be methoxycarbonyl, ethoxycarbonyl, propoxycarbonyl, isopropoxycarbonyl, butoxycarbonyl, pentoxycarbonyl, hexyloxycarbonyl, and all isomers thereof; $C_{1-6}$alkanoyloxy can be, for example, acetoxy, propanoyloxy, butanoyloxy, isobutanoyloxy, pentanoyloxy, hexanoyloxy, and all isomers thereof; aryl can be, for example, phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl or its N-oxide, thienyl, pyrimidinyl or its N-oxide, indolyl, isoquinolyl or its N-oxide, or quinolyl or its N-oxide, and all isomers thereof.

A specific value for $R^1$ is —H
Another value for $R^1$ is a hydroxyl protecting group.
A specific value for $R^1$ is of the formula —Si($R^{12}$)$_3$ wherein each $R^{12}$ can be independently $C_{1-4}$ alkyl.
A more specific value for $R^1$ is —Si(CH$_3$)$_3$.
Another specific value for $R^1$ is —Si(C$_4$H$_9$)$_3$.
A specific value for $R^2$ is hydroxyl protecting group.
A more specific value for $R^2$ is aroyl of the formula —C(=O)—Ar.
A more specific value for $R^2$ is p-methoxybenzoyl.
Another value for $R^2$ is —C(=O)—CR$_c$=C$_d$—Ar.
A more specific value for $R^2$ is (E)-cinnamoyl.
Another specific value for $R^2$ is (Z)-cinnamoyl.
A specific value for $R^3$ is a hydroxyl protecting group.
A more specific value for $R^3$ is alkyl.
Another more specific value for $R^3$ is cycloalkyl.
Another more specific value for $R^3$ is $C_6$cycloalkyl, that is, cyclohexyl.
A specific value for $R^4$ is an enolic hydroxyl protecting group.
A more specific value for $R^4$ is an alkanoyl.
Another more specific value for $R^4$ is acetyl.
Another more specific value for $R^4$ is propanoyl.
Another more specific value for $R^4$ is butanoyl.
A specific value for $R^6$ is a hydroxyl protecting group
A more specific value for $R^6$ is an —C(=O)—Ar.
Another more specific value for $R^6$ is a benzoyl.
Another more specific value for $R^6$ is a mono-methoxy substituted benzoyl.

Another more specific value for $R^6$ is a di-methoxy substituted benzoyl.

Another more specific value for $R^6$ is p-methoxy substituted benzoyl.

A specific value for X is a leaving group

A more specific value for X is —SAr.

Another more specific value for X is —SPh.

A specific value for —$OR^7$ is a leaving group.

A more specific value for —$OR^7$ is an acetamidate.

Another more specific value for —$OR^7$ is —OC(=NH)CCl$_3$.

A specific value for $R^8$ or $R^9$ is a hydroxyl protecting group.

A more specific value for $R^8$ or $R^9$ is an —C(=O)—Ar.

Another more specific value for $R^8$ or $R^9$ is a benzoyl.

Another more specific value for $R^8$ or $R^9$ is a monomethoxy substituted benzoyl.

Another more specific value for $R^8$ or $R^9$ is a di-methoxy substituted benzoyl.

Another more specific value for $R^8$ or $R^9$ is p-methoxy substituted benzoyl.

A specific value for $R^{10}$ is $C_{2-12}$ alkyl.

A more specific value for $R^{10}$ is —CH$_2$—CH(CH$_3$)$_2$.

A specific value for —$OR^{11}$ is a leaving group.

A more specific value for —$OR^{11}$ is an acetamidate.

Another more specific value for —$OR^{11}$ is —OC(=NH)CCl$_3$.

The invention also provides processes and intermediates useful for preparing compounds of formula (1). For example, intermediates useful for preparing a compound of the formula (1) wherein $R_1$ is hydrogen and $R_2$ is an aroyl or a cinnamoyl group, or a corresponding compound of the formula (1) wherein $R^1$ is a suitable protecting group, such as trialkylsilane. Thus the invention provides a compound of formula (1) wherein $R_2$ is both a suitable protecting group and is also desired in the final product such as an aroyl or a cinnamoyl group. Suitable protecting groups as used herein, as well as methods for their preparation and removal, are well known in the art, for example, see Greene, T. W.; Wutz, P. G. M. "Protecting Groups In Organic Synthesis" 3$^{rd}$ edition, 1999, New York, John Wiley & sons, Inc.

The invention also provides intermediate compounds, for example, of the formulas 6, 7, 9, 15, 18, 20, 25, 34, 35, and 36, among others, and as shown in accompanying preparative schemes hereinafter.

The invention also provides intermediate salts that are useful for preparing or purifying compounds of formula (1). Suitable methods for preparing salts are known in the art and are disclosed herein. As will be apparent to one skilled in the art, such salts can be converted to the corresponding free-base or to another salt using known methods.

The invention also provides a method for preparing a compound of formula (1) wherein $R^1$ is hydrogen comprising deprotecting a corresponding compound of formula (1) in the presence of a second protecting group $R^2$ wherein both $R^1$ and $R^2$ are suitable protecting groups, and as illustrated herein.

Compounds of the invention can generally be prepared using the illustrated synthetic schemes. Starting materials can be prepared by procedures described in these schemes, the accompanying experimental examples, or by procedures well known to one of ordinary skill in organic chemistry. The variables used in the schemes are as defined below or as in the claims.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal, for example, sodium, potassium or lithium, or alkaline earth metal, for example calcium, salts of carboxylic acids can also be made.

Useful dosages of the compounds of formula (1) can be determined by comparing their in vitro activity, and in vivo activity in animal models. Methods for the extrapolation of effective dosages in mice, and other animals, to humans are known to the art; for example, see U.S. Pat. No. 4,938,949.

DESCRIPTION OF PREFERRED EMBODIMENTS

The following examples in conjunction with the accompanying schemes and references provide illustrative and representative synthetic procedures for preparing compounds of the formula (1) and intermediate compounds leading thereto.

EXAMPLE I

Preparation of Compound 12

To a solution of 11 (4.20 g, 33.46 mmol) in dry THF (50 mL) was added n-BuLi (1.38 M, 27.4 mL, 37.8 mmol) at 0° C. The reaction was stirred at 0° C. for 20 min, then was cooled to −60° C. Isobutyl triflate (7.64 g, 37.06 mmol) in CH$_2$Cl$_2$ (10 mL) was added drop-wise. The reaction was allowed to gradually warmed up to 25° C. over 2 hours and stirred at 25° C. for 10 hours. Then 30 mL aqueous NaHCO$_3$ was added and THF was removed. The water layer was extracted with 30 mL hexane 4 times. The combined organic layer was washed with brine and dried over Na$_2$SO$_4$. The solvent was removed and the product was purified with Et$_3$N deactivated silica gel column chromatography to afford 12 (5.13 g, 85%).

EXAMPLE II

Preparation of Compound 13

To the solution of 12 (3.31 g, 21.80 mmol) and anhydrous methanol (0.706 mL, 17.44 mmol) in CH$_2$Cl$_2$ (50 mL) was added trimethylsilyl bromide (2.30 mL, 17.44 mmol) drop-wise at −40° C. The reaction solution was stirred at −40° C. for 10 min, then gradually warmed up to room temperature. The solvent was removed to afford 13 which was used without further purification.

EXAMPLE III

Preparation of Compound 14

To a solution of 10 (10 g, 34.7 mmol) and imidazole (2.83 g, 41.6 mmol) in CH$_2$Cl$_2$ (100 mL) was added tert-butylsilyl chloride (5.49 g, 36.4 mmol) at 25° C. The reaction solution was stirred at 25° C. for 12 hours and then quenched with saturated aqueous NaHCO$_3$. The organic layer was separated and the water layer was extracted with 50 mL CH$_2$Cl$_2$ three times. The combined organic layer was washed with brine and dried over Na$_2$SO$_4$. The solvent was removed and the product was purified by silica gel column chromatography to afford 14 (14.42 g, 99%).

EXAMPLE IV
Preparation of Compound 15

A mixture of ethyltriphenylphosphonium bromide (10 g, 27 mmol) and potassium tert-butoxide (1M in THF, 24.2 mL, 24.2 mmol) in anhydrous THF (30 mL) was stirred at 25° C. for 20 hours. Then 14 (3.95 g, 9.8 mmol) in anhydrous THF (10 mL) was added. After the reaction were stirred at 25° C. for two days, hexane (60 mL) and aqueous methanol (50%, 100 mL) was added. The organic layer was separated and the water layer was extracted with 30 mL hexane three times. The hexane layer was combined and the solvent was removed. The residue was dissolved in methanol (25 mL) and methyl iodide (1 mL, 16 mmol) was added. The solution was stirred at 25° C. for two hours. The solvent and excess methyl iodide were removed. The residue was partitioned between hexane (100 mL) and water (100 mL). The water layer was extracted with hexane (50 mL) twice and the combined hexane layer was dried over $Na_2SO_4$. The solvent was removed. The crude product was purified by silica gel column chromatography to afford 15 (3.98 g, 95%).

EXAMPLE V
Preparation of Compound 16

A solution of selenium dioxide (13 mg, 0.12 mmol) in $CH_2Cl_2$ (1 mL) was added tert-BuOOH (5M, 0.051 mL, 0.237 mmol) at 0° C. The solution was stirred at 0° C. for 15 min until the solid disappeared. 15 (99 mg, 0.234 mmol) was added in one portion. The reaction solution was stirred at 0° C. for 5 hours. The reaction was diluted with 2 mL $CH_2Cl_2$ and then quenched with 2 mL aqueous $Na_2SO_3$. The organic layer was separated and the water layer was extracted with 3 mL $CH_2Cl_2$ three times. The combined organic layer was washed with brine and dried with $Na_2SO_4$. The solvent was removed and the product was purified by silica gel column chromatography to afford 16 (100.5 mg, 99%).

EXAMPLE VI
Preparation of Compound 9

To a solution of DMSO (0.016 mL, 0.23 mmol) in dry $CH_2Cl_2$ (0.5 mL) was added oxalyl chloride (0.01 mL, 0.115 mmol) in −50° C., and the solution was stirred at −50° C. for 3 min. 16 (41.1 mg, 0.095 mmol) in $CH_2Cl_2$ (0.3 mL) was added. The flask was washed with $CH_2Cl_2$ once. The reaction was stirred at −50° C. for 30 min, then $Et_3N$ (0.066 mL, 0.48 mmol) was added. The reaction was stirred at −50° C. for 10 min, then was allowed to warm up to 25° C. Water (2 mL) was added and the organic layer was separated. The water layer was extracted with 3 mL $CH_2Cl_2$ for three times. The combined organic layer was washed with brine and dried with $Na_2SO_4$. The solvent was removed and the product was purified by silica gel column chromatography to afford 9 (40.4 mg, 99%).

EXAMPLE VII
Preparation of Compounds 17, 18, 19

A solution of 13 (17.44 mmol) in dry ether (60 mL) and dry THF (10 mL) was cooled to −78° C., then tert-BuLi (1.71M, 20.4 mL, 34.88 mmol) was added drop-wise. The reaction was stirred at −78° C. for 30 min, and was then cannulated to a clear solution of CuCN (781 mg, 8.72 mmol) and LiCl (740 mg, 17.44 mmol) in THF (20 mL, CuCN and LiCl was stirred for 10 min at 25° C.) at −78° C. After the solution was stirred at −78° C. for 20 min, a solution of 9 (1.22 g, 2.85 mmol) and trimethylsilyl chloride (redistilled, 1.8 mL, 14.25 mmol) in THF (5 mL) was cannulated to the cuprate solution in −78° C. The reaction solution was stirred at −78° C. for 30 min, then was allowed to gradually warmed up to 25° C. To the reaction was added 1 mL triethylamine and diluted with 50 mL hexane. The solution was passed through a short silica gel pad which was pretreated with 5% triethylamine-hexane. The silica gel was washed with ether (10 mL) three times. The solvent was removed to afford crude product 17. Crude 17 was dissolved in 10 mL anhydrous benzene and the benzene was removed. This operation was repeated three times. The reaction mixture was vacuumed for 30 min and then it was dissolved in anhydrous THF (20 mL). Potassium tert-butoxide (1M, 3.42 mL, 3.42 mmol) was added at 0° C. The reaction solution was stirred at 0° C. for 10 min, then was cooled to −30° C. Acetyl chloride (redistilled, 0.3 mL, 4.28 mmol) was added drop-wise. The reaction was stirred at −30° C. for 30 min, and was then allowed to warm up to 25° C. Saturated aqueous $NaHCO_3$ (20 mL) and ethyl acetate (20 mL) were added. The organic layer was separated and the water layer was extracted with 10 mL ethyl acetate three times. The combined organic layer was washed with brine and dried over $Na_2SO_4$. The solvent was removed and the product was purified by silica gel column chromatography to afford 18 which was still contaminated by some impurity. 60.5 mg of purified 18 was removed for an NMR experiment and the rest of the product was carefully dried and dissolved in anhydrous $CH_2Cl_2$ (30 mL). Anhydrous ethylene glycol (0.769 mL, 13.8 mmol) and PPTS (pyridinium p-toluenesulfonate), (30 mg) were added. The reaction was stirred under nitrogen at 25° C. for 3 hours until the disappearance of 18 on TLC. Triethylamine (0.2 mL) and water (20 mL) were added. The organic layer was separated and the water layer was extracted with $CH_2Cl_2$ (10 mL) three times. The combined organic layer was washed with brine and dried with $Na_2SO_4$. The solvent was removed and the product was purified with silica gel column chromatography to afford 19 (1.274 g, 75% from 9).

EXAMPLE VIII
Preparation of Compound 20

To a solution of 19 (118.9 mg, 0.193 mmol) in anhydrous THF (1 mL) was added potassium tert-butoxide (1M, 0.3 mL, 0.3 mmol) at 0° C. After the reaction was stirred at 0° C. for 10 min and cooled to −78° C., it was cannulated to a solution of Davis reagent (87 mg, 0.325 mmol) in anhydrous THF (0.5 mL) in −78° C. The flask was rinsed with THF (0.3 mL) once. The reaction was stirred at −78° C. for 30 min, then 30 mg silica gel was added in −78° C. before it was warmed up to 25° C. The silica gel was filtered and solvent was removed. The product was purified by silica gel chromatography to give 20 (86 mg, 76%).

EXAMPLE IX
Preparation of Compound 7

A solution of 20 (83.4 mg, 0.142 mmol) in anhydrous THF (1 mL) was added $LiAiH_4$ (1M, 0.071 mL, 0.071 mmol) at −78° C. The reaction solution was stirred at −78° C. for 1 hour and was quenched with ethyl acetate. Saturated aqueous potassium sodium tartrate (3 mL) was added. The organic layer was separated and the water layer was extracted with ethyl acetate (3 mL) for three times. The combined organic layer was washed with brine and dried over $Na_2SO_4$. The solvent was removed and the product was purified with silica gel column chromatography to afford 7 (84.1 mg, 99%).

EXAMPLE X
Preparation of Compound 22

Dry 1,2,3,4-O-tetraacetyl-L-arabinose (18.3 g, 57.5 mmol) was dissolved in dry $CH_2Cl_2$ (200 mL) and was cooled to −78° C. Thiophenol (6.5 mL, 63.3 mmol) was added followed by addition of $SnCl_4$ (1M, 17.3 mL, 17.3 mmol). The reaction solution was stirred at −78° C. for 6 hours until the disappearance of the starting material in TLC. Saturated aqueous $NaHCO_3$ (100 mL) was added. The organic layer was separated and the water layer was extracted with $CH_2Cl_2$ (30 mL) three times. The combined organic layer was washed with brine and dried over $Na_2SO_4$. The solvent was removed and the product was purified by silica gel column chromatography to afford thiophenyl-2,3,4-O-triacetyl-L-arabinose (16.95 g, 80%). Thiophenyl-2,3,4-O-triacetyl-L-arabinose (8.88 g, 24.1 mmol) was dissolved in MeOH (120 mL) followed by the addition of sodium methoxide (65 mg, 2 mmol ). The reaction solution was stirred at 25° C. for three hours, then saturated aqueous $NH_4Cl$ was added. The organic layer was separated and the water layer was extracted with $CH_2Cl_2$ (30 mL) three times. The combined organic layer was washed with brine and dried over $Na_2SO_4$. The solvent was removed and the product was purified by silica gel column chromatography to afford 22 (5.53 g, 22.9 mmol, 95%)

EXAMPLE XI
Preparation of Compounds 23, 24

A solution of 22 (4.85 g, 20.04 mmol) in $CH_2Cl_2$ (100 mL) was added 2,2-dimethoxypropane (2.96 mL, 24.05 mmol) and CSA (camphor sulfonic acid) (30 mg) at 25° C. The reaction solution was stirred at 25° C. for 30 min and was quenched with saturated aqueous $NaHCO_3$ (30 mL). The organic layer was separated and the water layer was extracted with $CH_2Cl_2$ (20 mL) three times. The combined organic layer was washed with brine and dried over $Na_2SO_4$. The solvent was removed and the reaction mixture was carefully dried and was dissolved in $CH_2Cl_2$ (100 mL). Triethylamine (4.2 mL, 30 mmol), acetyl anhydride (2.26 mL, 24 mmol), and DMAP (50 mg) were added. The reaction was stirred at 25° C. for two hours, then was quenched with saturated aqueous $NaHCO_3$ (30 mL). The organic layer was separated and the water layer was extracted with 30 mL $CH_2Cl_2$ for three times. The combined organic layer was washed with brine and dried over $Na_2SO_4$. The solvent was removed and the product was dissolved in methanol (100 mL) followed by addition of AMBERLITE IR-118H (4 g). The reaction was stirred at 25° C. for 12 hours and the solid was filtered. The solvent was removed and the product was purified by silica gel chromatography afforded 24 (5.1 g, 90% from 22).

EXAMPLE XII
Preparation of Compound 25

A solution of 24 (2.22 g, 7.81 mmol) and 2,6-lutidine (1.8 mL, 15.62 mmol) in anhydrous $CH_2Cl_2$ (260 mL) was cooled to −60° C. Triethylsilyl triflate (2.1 mL, 9.37 mmol) was added drop-wise. The reaction was stirred at −60° C. for one hour and at −70° C. for another one hour. The reaction was quenched with saturated aqueous $NaHCO_3$ (50 mL) at −70° C. and was allowed to warm up to 25° C. The organic layer was separated and the water layer was extracted with $CH_2Cl_2$ (30 mL) for three times. The combined organic layer was washed with brine and dried over $Na_2SO_4$. The solvent was removed and the product was purified with silica gel column chromatography to afford 25 (2.8 g, 90%).

EXAMPLE XIII
Preparation of Compound 27

Dry 1,2,3,4-O-tetraacetyl-D-xylose (33.4 g, 104.9 mmol) was dissolved in dry $CH_2Cl_2$ and was cooled to 0° C. HBr (30% in AcOH, 80 mL) was added slowly by addition funnel. The reaction was stirred at 0° C. for one hour and at 25° C. for three hours. The reaction solution was washed first with water (50 mL), then the organic layer was poured into cold saturated aqueous $NaHCO_3$ with stirring. The organic layer was separated and the water layer was extracted with $CH_2Cl_2$ (50 mL) three times. The combined organic layer was washed with brine and dried over $Na_2SO_4$. The solvent was removed to afford 27 (33.088 g, 93%).

EXAMPLE XIV
Preparation of Compound 28

Carefully dried 27 (8.5 g, 23.94 mmol) was dissolved in dry nitromethane (30 mL, distilled over $CaH_2$) and thioethanol (3.55 mL, 47.89 mmol) and 2,6-lutidine (4.2 mL, 35.91 mmol, distilled over $CaH_2$) was added. The reaction solution was stirred under nitrogen at 25° C. for 12 hours. The reaction was quenched with saturated aqueous $NaHCO_3$. The organic layer was separated and the water layer was extracted with $CH_2Cl_2$ (30 mL) for three times. The combined organic layer was washed with brine and dried with $Na_2SO_4$. The solvent was removed and the product was purified by silica gel column chromatography to afford 28 (6.29 g, 82%).

EXAMPLE XV
Preparation of Compound 29

To a solution of 28 (3.679 g, 11.48 mmol) in methanol (60 mL) was added sodium methoxide (30 mg, 0.57 mmol). The reaction solution was stirred at 25° C. for 1 hour and methanol was removed to afforded 29 (2.750 g, 99%) which was used in the next step without further purification.

EXAMPLE XVI
Preparation of Compound 30

To a solution of 29 (2.714 g, 11.48 mmol) in dry THF (100 mL) was added NaH (60% in mineral oil, 1.45 g, 36 mmol) at 0° C. The reaction solution was stirred at 25° C. for 10 min and p-methoxybenzyl chloride (3.3 mL, 24.3 mmol) and tetrabutylammonium iodide (100 mg, 0.27 mmol) were added. The reaction was stirred under reflux for 4 hours and quenched with saturated aqueous $NaHCO_3$. The organic layer was separated and the water layer was extracted with ethyl acetate (30 mL) three times. The combined organic layer was washed with brine and dried over $Na_2SO_4$. The solvent was removed and the product was purified by silica gel column chromatography to afford 30 (5.14 g, 98%).

EXAMPLE XVII
Preparation of Compounds 31, 32

To a solution of carefully dried 30 (3.73 g, 8.17 mmol) in dry $CH_2Cl_2$ (20 mL) was added zinc chloride (1M in ether, 0.5 mL, 0.5 mmol) at −60° C. The reaction was stirred at −60° C. for 30 min and was warmed up to 0° C. in 30 min. The reaction was quenched with saturated aqueous $NaHCO_3$. The organic layer was separated and the water layer was extracted with $CH_2Cl_2$ (15 mL) three times. The combined organic layer was washed with brine and dried over $Na_2SO_4$. The solvent was removed to afford crude product 31. The crude 31 was dissolved in methanol (40 mL) and sodium methoxide (22 mg, 0.4 mmol) was added. The reaction was stirred at 25° C. for 4 hours. The solvent was removed and the product was purified by silica gel column chromatography to afford 32 (3.4 g, 96% from 30).

EXAMPLE XVIII
Preparation of Compound 33

To a solution of 32 (3.2 g, 7.36 mmol) and triethylamine (1.54 mL, 11.04 mmol) in $CH_2Cl_2$ (20 mL) was added 4-methoxybenzoyl chloride (1.33 mL, 9.57 mmol) and DMAP (45 mg, 0.37 mmol). The reaction was stirred at 25° C. for 48 hours. A small amount of reaction solution was taken out, quenched with saturated aqueous NaHCO$_3$ and diluted with 1 mL CH$_2$Cl$_2$. The organic layer was separated and the solvent was removed. The crude mixture was checked with $^1$H-NMR. When the NMR signal of 32 disappeared, the reaction was quenched with saturated aqueous NaHCO$_3$. The organic layer was separated and the water layer was extracted with CH$_2$Cl$_2$ (30 mL) three times. The combined organic layer was washed with brine and dried over Na$_2$SO$_4$. The solvent was removed and the product was purified with silica gel column chromatography to afford 33 (4.06 g. 97%).

EXAMPLE XIX
Preparation of Compound 34
To a solution of 33 (2.31 g, 4.06 mmol) in CH$_2$Cl$_2$ (25 mL) and water (3 mL) was added NBS (0.795 g, 4.46 mmol) in one portion. After the reaction was stirred at 25° C. for 1 hour, saturated aqueous Na$_2$SO$_3$ was added. The organic layer was separated and the water layer was extracted with CH$_2$Cl$_2$ (15 mL) three times. The combined organic layer was washed with brine and dried with Na$_2$SO$_4$. The solvent was removed and the product was purified with silica gel column chromatography to afford 3,4-di-O-(4-methoxybenzyl)-2-O-(4-methoxybenzoyl)-α/β-D-xylopyranose (1.87 g, 88%). Carefully dried 3,4-di-O-(4-methoxybenzyl)-2-O-(4-methoxybenzoyl)-α/β-D-xylopyranose (413.3 mg, 0.788 mmol) was dissolved in dry CH$_2$Cl$_2$ (4 mL) and trichloroacetonitrile (0.4 mL, 3.94 mmol) and DBU (1 drop) were added. The reaction was stirred at 25° C. for 12 hours. The solvent was removed and the product was purified by silica gel column chromatography to afforded 34 (555 mg, 95%).

EXAMPLE XX
Preparation of Compound 35
A solution of carefully dried 25 (339 mg, 0.718 mmol), 34 (941 mg, 1.407 mmol) and molecular sieve 4A powder (150 mg) in dry CH$_2$Cl$_2$ (3 mL) was stirred at 25° C. for 15 min, then was cooled to −78° C. BF$_3$-Et(0.1 M in CH$_2$Cl$_2$, 0.7 mL, 0.07 mmol) was added. The reaction was gradually warmed up to −40 ° C. and was stirred at −40° C. for 2 hours. Et$_3$N (0.1 mL) was added and the reaction solution was filtered. The solvent was removed and the product was purified by silica gel column chromatography to afford 35 (602 mg, 93%).

EXAMPLE XXI
Preparation of Compound 6
To a solution of 35 (129 mg, 0.143 mmol) in CH$_2$Cl$_2$—H$_2$O (2 mL, 10:1) was added NBS (31 mg, 0.172 mmol). The reaction was stirred at 25° C. for two hours and then was quenched with saturated aqueous Na$_2$SO$_3$. The organic layer was separated and the water layer was extracted with CH$_2$Cl$_2$ (3 mL) three times. The combined organic layer was washed with brine and dried over Na$_2$SO$_4$. The solvent was removed and the product was purified with silica gel column chromatography to afford 2-O-acetyl-3-O-(3,4-di-O-(4-methoxybenzyl)-2-O-(4-methoxybenzoyl)-β-D-Xylopyranosyl)-4-O-(triethylsilyl)-β-L-arabinopyranose (93.4 mg, 81%). To a solution of 2-O-acetyl-3-O-(3,4-di-O-(4-methoxybenzyl)-2-O-(4-methoxybenzoyl)-β-D-xylopyranosyl)-4-O-(triethylsilyl)-β-L-arabinopyranose in dry CH$_2$Cl$_2$ (2 mL) was added trichloroacetonitrile (0.068 mL, 0.575 mmol) and DBU (1 drop). The reaction was stirred at 25° C. for 12 hours and the solvent was then removed. The product was purified by Et$_3$N deactivated silica gel column chromatography to afford 6 (96.8 mg, 88%).

EXAMPLE XXII
Preparation of Compound 36
A solution of 6 (15.3 mg, 0.026 mmol), 7 (58 mg, 0.061 mmol) and dry molecular sieve 4 Å powder (about 30 mg) in dry CH$_2$Cl$_2$ (0.7 mL) was stirred at 25° C. for 15 min, then was cooled to −20° C. TMSOTf (0.02 M in CH$_2$Cl$_2$, 0.16 mL, 0.0032 mmol) was added. The reaction was stirred at −20° C. for 5 hours and was quenched with 0.1 mL Et$_3$N. The solid was filtered and the solvent was removed. The product was purified with Et$_3$N deactivated silica gel column chromatography to afford 36 (30.1 mg, 89%).

EXAMPLE XXIII
Preparation of OSW-1(1)
To a solution of 36 (16.5 mg, 0.012 mmol) in CH$_2$Cl$_2$—H$_2$O (1 mL, 10:1) was added DDQ (8.1 mg, 0.036 mmol). The reaction mixture was stirred at 25° C. for 12 hours, then the CH$_2$Cl$_2$ was removed and acetone (1 mL) and Pd(CN)$_2$Cl$_2$ (0.5 mg) was added. After the reaction was stirred at 25° C. for 2 hours, the solvent was removed and the product was purified by preparative TLC to afford 1 (8.5 mg, 81%).

All cited publications, patents, and patent documents are incorporated by reference herein in their entirety. The invention has been described with reference to various specific and preferred embodiments and techniques. However, it should be understood that many variations and modifications may be made while remaining within the spirit and scope of the invention.

What is claimed is:

1. A process for preparing a saponin intermediate comprising:

reacting, in the presence of a 1,4-addition activating agent, a compound of the formula (9)

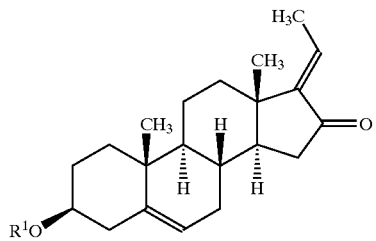

9 wherein R$^1$ is independently —H or a hydroxyl protecting group, with an alpha-alkoxy vinyl cuprate compound of the formula (8)

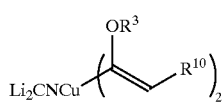

8 wherein R$^3$ is an enolic hydroxyl protecting group and R$^{10}$ is C$_{2-12}$ alkyl, to form a compound of the formula (18):

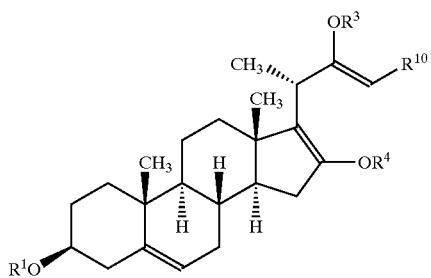

wherein R⁴ is an enolic hydroxyl protecting group.

2. The process of claim 1, wherein $R^{10}$ is —$C_{2-6}$ alkyl.

3. The process of claim 2, wherein $R^{10}$ is —$CH_2$—$CH(CH_3)_2$.

4. The process of claim 1, further comprising:

a) converting the vinyl ether of compound (18) at —$OR^3$ to a corresponding ketal;

b) generating a corresponding enolate at $R^4$ of compound (18) wherein $R^4$ is a metal counter ion; and c) oxidizing the resulting enolate to an alpha-hydroxy ketone compound of the formula (20):

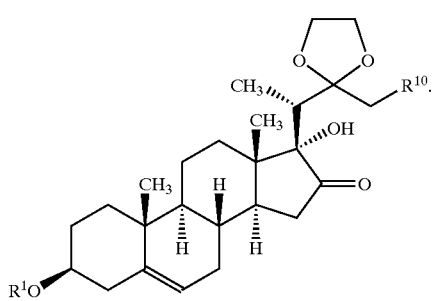

5. The process of claim 4, wherein $R^{10}$ is $C_{2-6}$ alkyl.

6. The process of claim 5, wherein $R^{10}$ is —$CH_2$—$CH(CH_3)_2$.

7. The process of claim 1, further comprising: stereoselectively reducing the ketone of the formula (20) to a diol compound of formula (7):

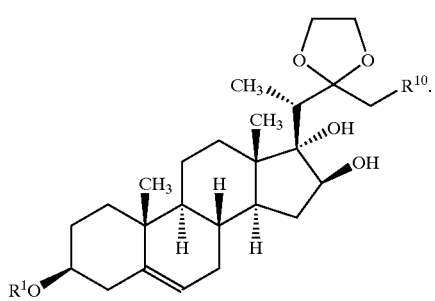

8. The process of claim 7, wherein $R^{10}$ is —$C_{2-6}$ alkyl.

9. The process of claim 8, wherein $R^{10}$ is —$CH_2$—$CH(CH_3)_2$.

10. A process of claim 7, further comprising preparing a compound of formula (1)

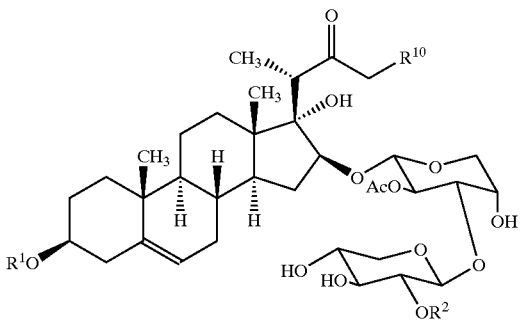

wherein $R^1$ is independently H or a hydroxyl protecting group, and $R^2$ is independently —C(=O)—Ar or —C(=O)—$CR_c$=$CR_d$—Ar, wherein Ar is independently aryl or heteroaryl, and $R_c$ and $R_d$ are each independently —H, $C_{1-6}$alkyl, $C_{1-6}$alkanoyl, $C_{1-6}$alkoxycarbonyl, aryl, (aryl)$C_{1-6}$alkyl, arylcarbonyl, or aryloxycarbonyl, and $R^{10}$ is $C_{2-12}$alkyl, comprising:

a) coupling a compound of the formula (7):

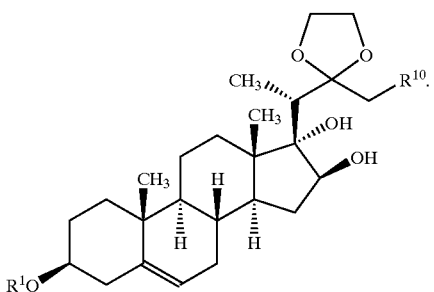

with a compound of the formula (6):

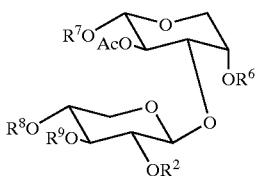

wherein $R^6$, $R^8$ and $R^9$ are each independently a hydroxyl protecting group, and —$OR^7$ is a leaving group; to form a compound of the formula (36); and

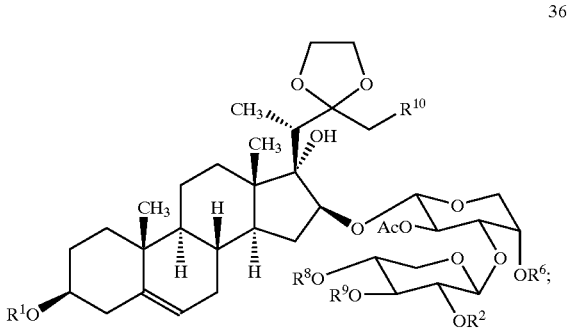

b) deprotecting the compound of formula (36) to afford the compound of formula (1).

11. The process of claim 10, wherein $R^{10}$ is —$C_{2-6}$alkyl.

12. The process of claim 11, wherein $R^{10}$ is —$CH_2$—CH($CH_3$)$_2$.

13. The process of claim 10, wherein $R^1$ as a hydroxyl protecting group is of the formula —Si($R^{12}$)$_3$ wherein each $R^{12}$ is independently $C_{1-4}$alkyl.

14. The process of claim 10, wherein the Ar of —C(=O)—Ar is independently aryl or heteroaryl, optionally substituted with one or more substituents independently selected from halo, —OH, —CN, —$NO_2$, —$CF_3$, —$OCF_3$, methylene dioxy, $C_{1-6}$alkyl, $C_{1-6}$alkoxy, phenyl, $NR_cR_d$, or —C(=O)$NR_cR_d$; wherein each $R_c$ and $R_d$ is independently hydrogen, $C_{1-6}$alkyl, $C_{1-6}$alkanoyl, $C_{1-6}$alkoxycarbonyl, aryl, (aryl)$C_{1-6}$alkyl, arylcarbonyl, or aryloxycarbonyl; or $R_c$ and $R_d$ together with the nitrogen to which they are attached form a pyrrolidino, piperidino, morpholino, or thiomorpholino ring; or a pharmaceutically acceptable salt thereof.

15. The process of claim 10, wherein the Ar of —C(=O)—$CR_c$=$CR_d$—Ar is independently aryl or heteroaryl, optionally substituted with one or more substituents independently selected from halo, —OH, —CN, —$NO_2$, —$CF_3$, —$OCF_3$, methylene dioxy, $C_{1-6}$alkyl, $C_{1-6}$alkoxy, phenyl, $NR_cR_d$, or —C(=O)$NR_cR_d$; wherein each $R_c$ and $R_d$ is independently hydrogen, $C_{1-6}$alkyl, $C_{1-6}$alkanoyl, $C_{1-6}$alkoxycarbonyl, aryl, (aryl)$C_{1-6}$alkyl, arylcarbonyl, or aryloxycarbonyl; or $R_c$ and $R_d$ together with the nitrogen to which they are attached form a pyrrolidino, piperidino, morpholino, or thiomorpholino ring; or a pharmaceutically acceptable salt thereof.

16. The process of claim 10, wherein $R^2$ is independently p-methoxybenzoyl, 3,4-dimethoxybenzoyl, (E)-cinnamoyl, or (Z)-cinnamoyl.

17. The process of claim 10, wherein $R^1$ is H, and $R^2$ is p-methoxybenzoyl.

18. The process of claim 1, wherein the 1,4-addition activating agent is trimethylsilylchloride, the $R^3$ enolic hydroxyl protecting group is —$C_{5-7}$ cycloalkyl, and the $R^4$ enolic hydroxyl protecting group is alkanoyl.

19. The process of claim 10, wherein the deprotecting to afford the compound of formula (1) comprises sequentially treating the compound of formula (36) with DDQ and bis-(acetonitrile)dichloropalladium(II).

20. The process of claim 1, wherein the compound of the formula (9) is prepared by the steps comprising:

a) olefinating the ketone of the compound of formula (14);

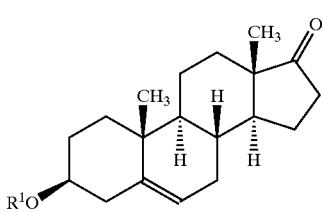

14 wherein $R^1$ is independently —H or a hydroxyl protecting group, b) allylicly oxidizing the resulting olefin compound to form an allylic alcohol compound of formula (15); and

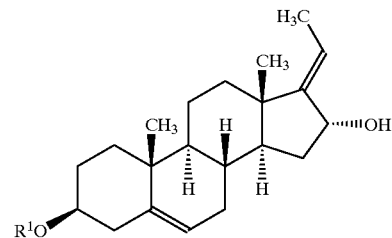

15 c) oxidizing the allylic alcohol (15) to form a 1,4-enone compound of formula (9):

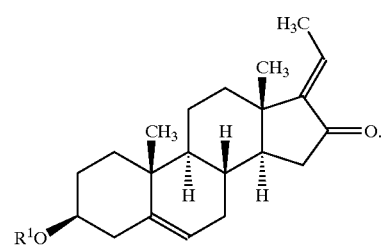

9

21. The process of claim 10, wherein the compound of the formula (6)

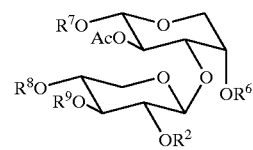

6 is prepared by the steps comprising:

a) glycosylating a compound of the formula (25)

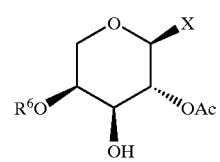

25 wherein $R^6$ is a hydroxyl protecting group and X is an $SN_1$ leaving group; with a compound of the formula (34):

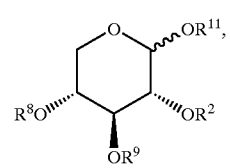

34 wherein —$OR^{11}$ is —OC(=NH)$CCl_3$, to afford a compound of the formula (35); and

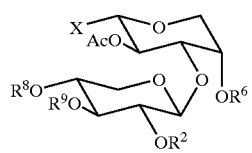
b) converting X into a leaving group —OR$^7$ of the formula —O—C(=NH)CCl$_3$ to afford the compound of formula (6).
22. The process of claim 21, wherein the leaving group X is —SAr.
* * * * *

UNITED STATES PATENT AND TRADEMARK OFFICE
CERTIFICATE OF CORRECTION

PATENT NO.       : 6,753,414 B2  
APPLICATION NO. : 10/213363  
DATED            : June 22, 2004  
INVENTOR(S)     : Jin et al.

It is certified that error appears in the above-identified patent and that said Letters Patent is hereby corrected as shown below:

In column 5, line 36, after "$R^8$" insert -- , --.

In column 8, lines 1-9, formula 35, delete " 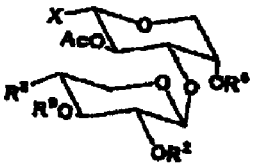 " and insert

-- 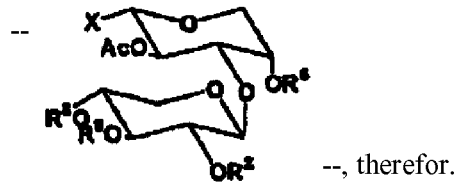 --, therefor.

In column 10, line 41, delete "99%:" and insert -- 99%; --, therefor.

In column 12, formula 7, delete " 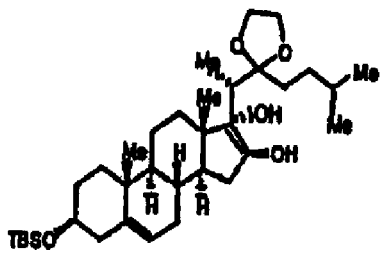 " and insert

-- 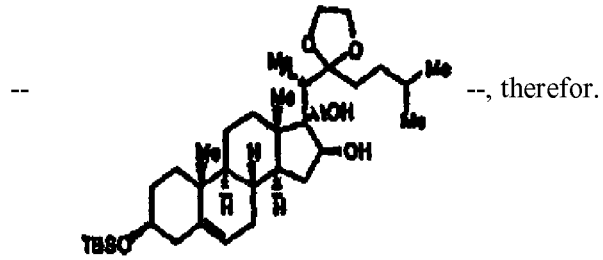 --, therefor.

UNITED STATES PATENT AND TRADEMARK OFFICE
CERTIFICATE OF CORRECTION

PATENT NO. : 6,753,414 B2
APPLICATION NO. : 10/213363
DATED : June 22, 2004
INVENTOR(S) : Jin et al.

It is certified that error appears in the above-identified patent and that said Letters Patent is hereby corrected as shown below:

In columns 11-12, formula 20, delete " 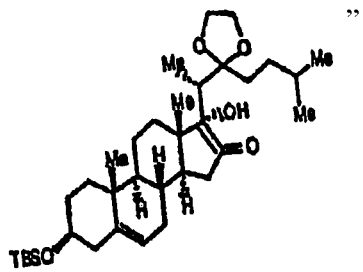 "

and insert -- 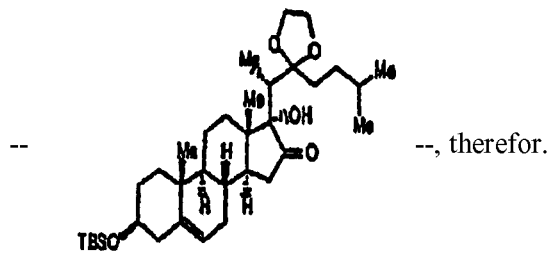 --, therefor.

In column 11, line 31, delete "0.5 h." and insert -- 0.5 h, --, therefor.

In column 26, line 48, after "$R^8$" insert -- , --.

Signed and Sealed this

Twenty-ninth Day of July, 2008

JON W. DUDAS
*Director of the United States Patent and Trademark Office*